United States Patent [19]

Volk

[11] Patent Number: 4,710,193

[45] Date of Patent: Dec. 1, 1987

[54] ACCOMMODATING INTRAOCULAR LENS AND LENS SERIES AND METHOD OF LENS SELECTION

[76] Inventor: David Volk, 3336 Kersdale Rd., Pepper Pike, Ohio 44124

[21] Appl. No.: 897,656

[22] Filed: Aug. 18, 1986

[51] Int. Cl.$^4$ .............................................. A61F 2/16
[52] U.S. Cl. ........................................ 623/6; 351/161
[58] Field of Search .................... 623/6; 351/160, 161

[56] References Cited

U.S. PATENT DOCUMENTS 4,504,982  3/1985  Burk ....................................... 623/6

OTHER PUBLICATIONS

"Problems and Compromises in the Design of Aspheric Cataract Lenses", by John K. Davis, American Journal of Optometry and Archives of American Academy of Optometry, vol. 36, No. 6, Jun. 1959, pp. 279-288.

Primary Examiner—Ronald L. Frinks
Attorney, Agent, or Firm—Baldwin, Egan, Hudak & Fetzer

[57] ABSTRACT

This invention relates to an improved aspheric posterior chamber intraocular lens and lens series of said novel intraocular lens, which lens is used as a replacement within the eye for the absent human crystalline lens, and a simplified method of selecting a lens from said lens series for use in a given eye. The novel lens of this invention is designed to have a continuously and regularly increasing refractive power from its axis peripheralward in its optically active area and to achieve the following results: the correction of the axial refractive error of the aphakic eye in which it is placed, and the production of clear central vision over a continuous range of distances from far to near, where far is defined as six meters and beyond, and near or reading distance is defined as generally 40 cm from the eye but may be as close as 33 cm.

15 Claims, 9 Drawing Figures

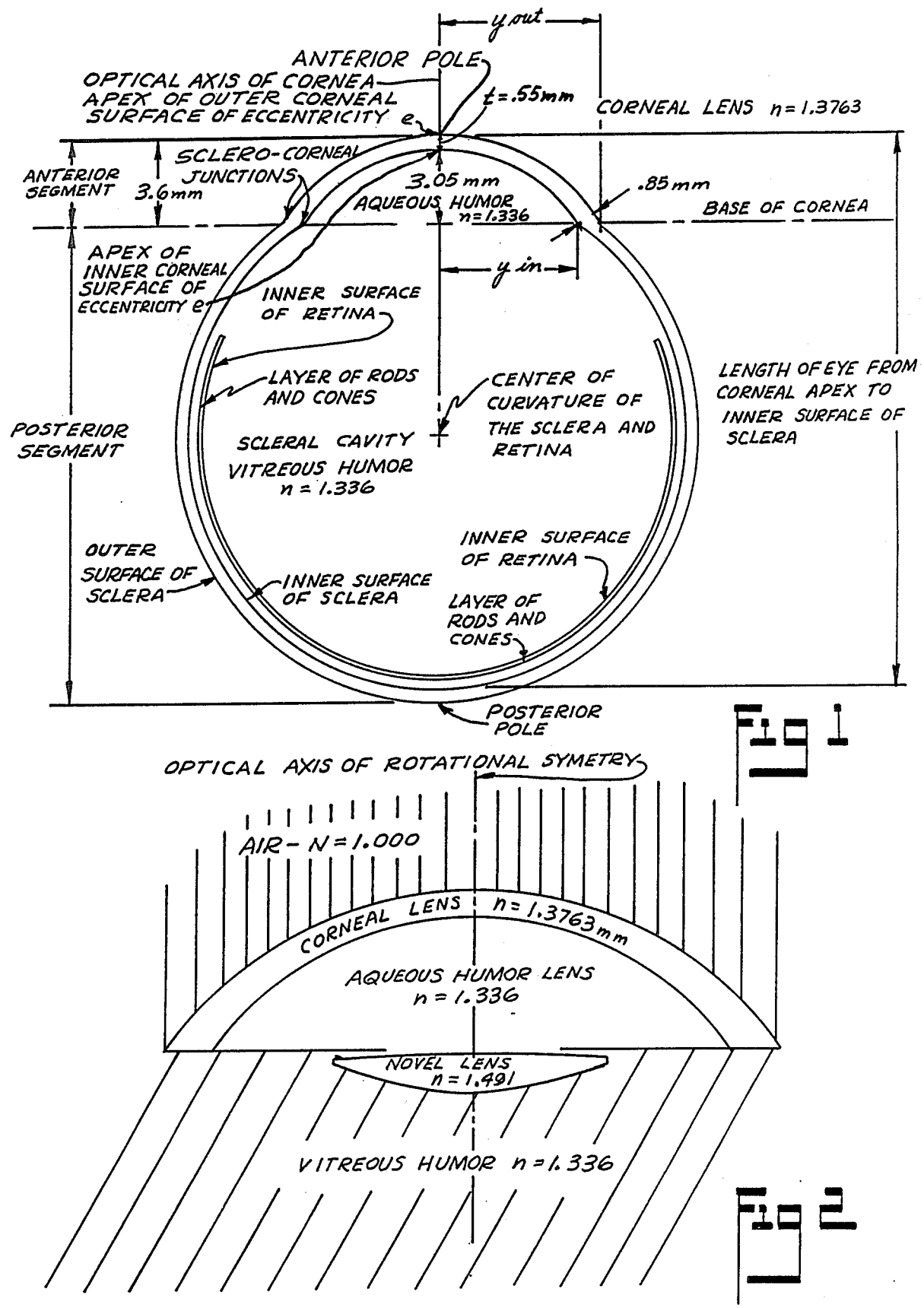

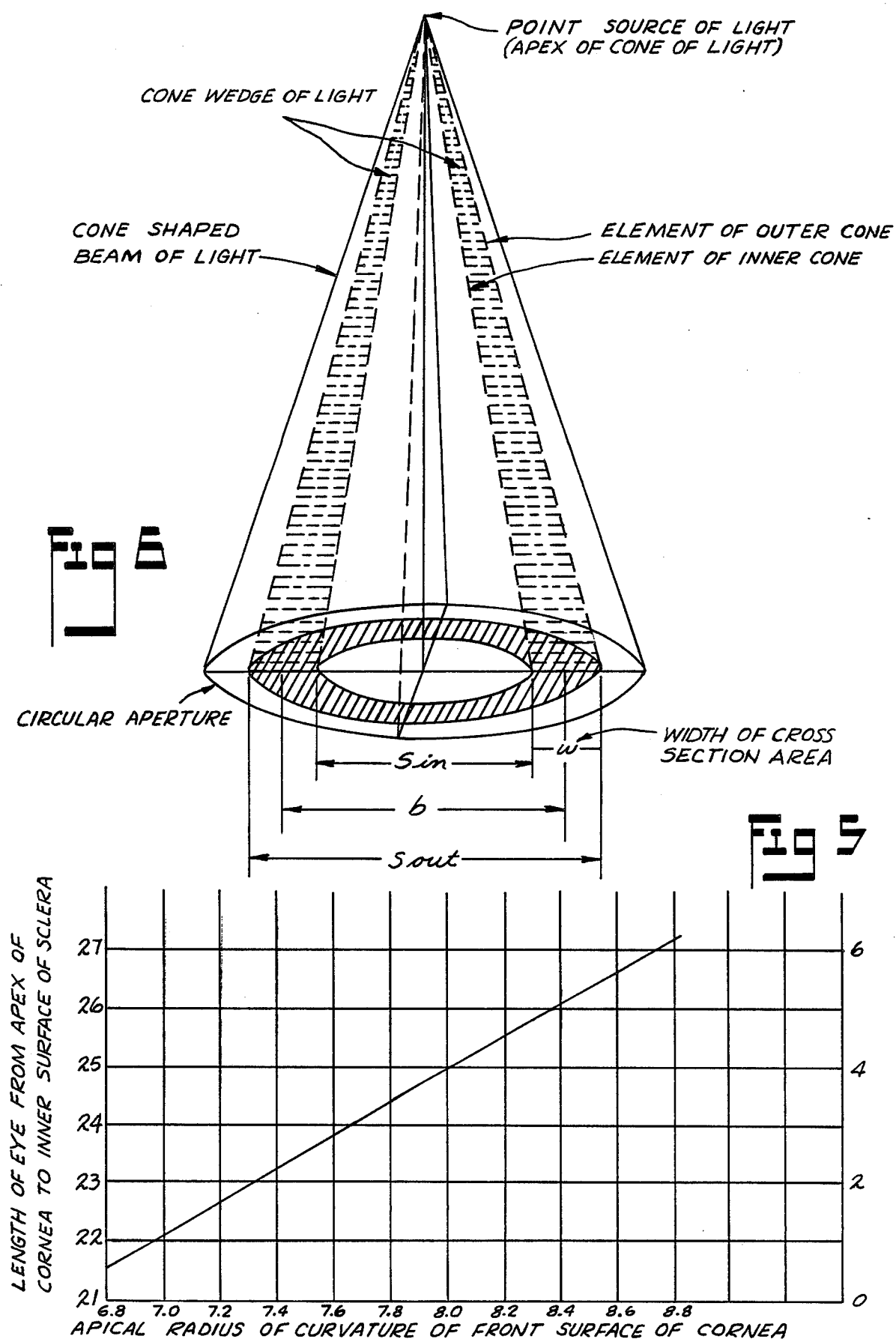

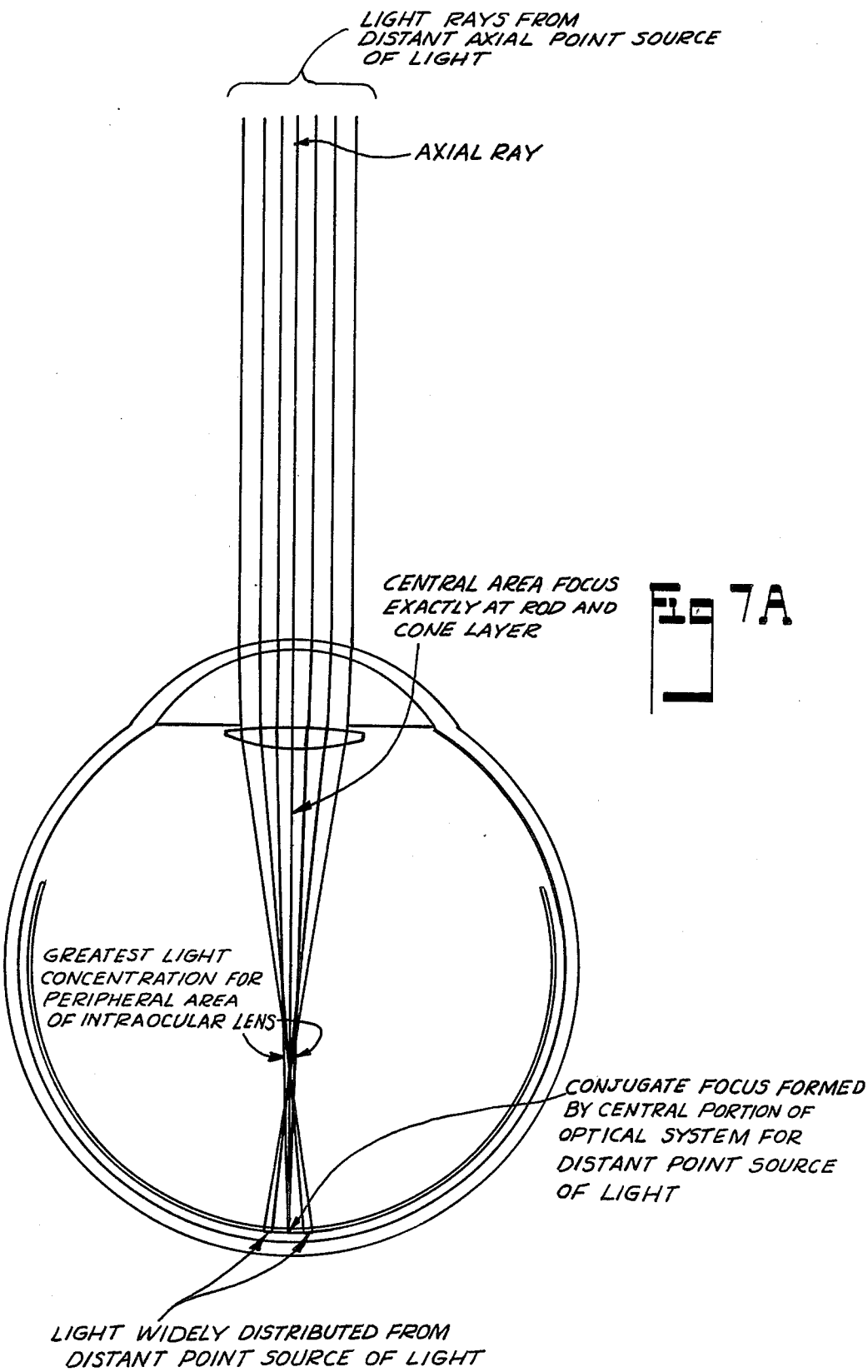

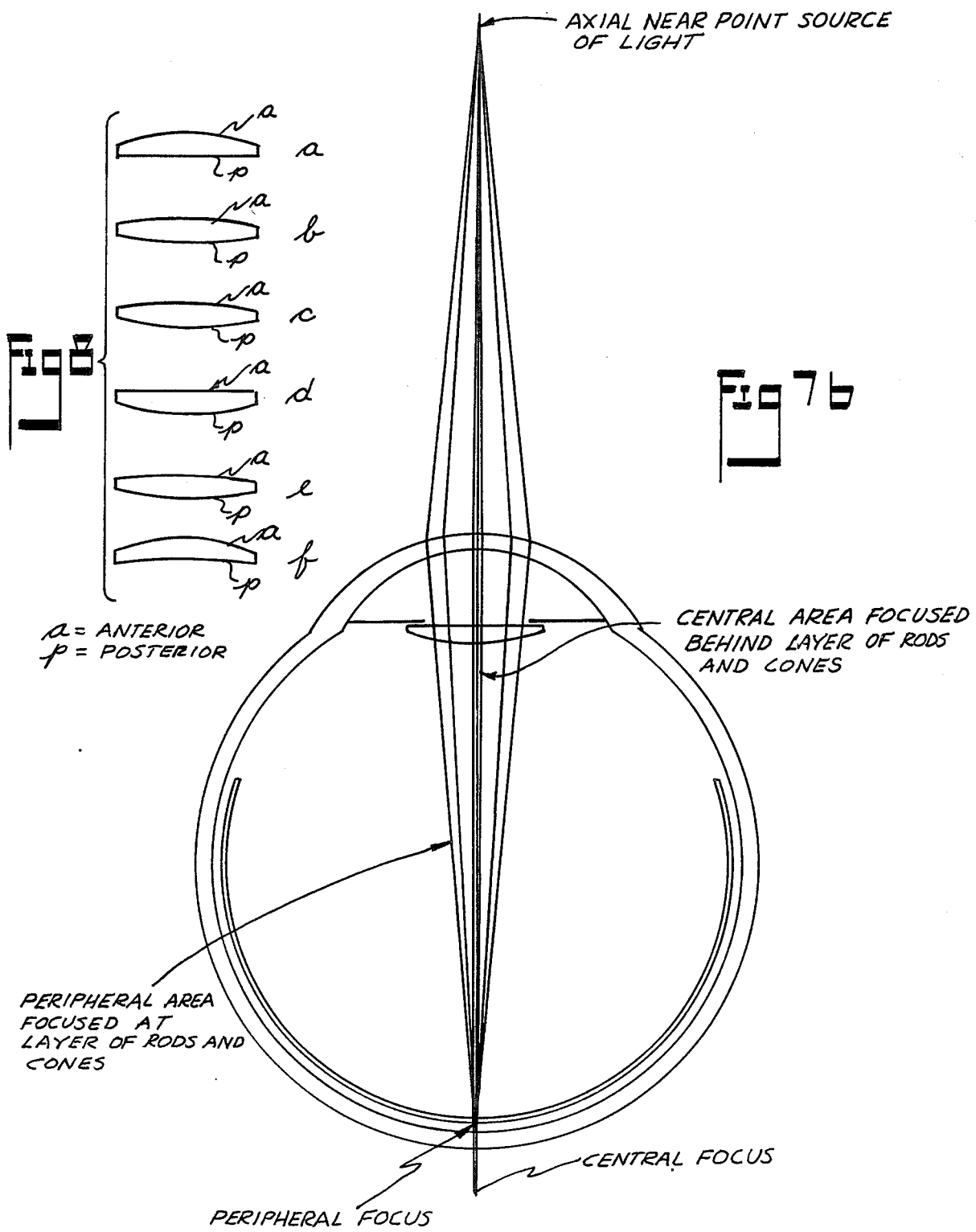

ACCOMMODATING INTRAOCULAR LENS AND LENS SERIES AND METHOD OF LENS SELECTION

This invention relates to an improved aspheric intraocular lens and lens series of said novel intraocular lens, which lens is used as a replacement within the eye for the absent human crystalline lens, and a simplified method of selecting a lens from said lens series of the novel lens of this invention for use in a given eye.

An intraocular lens is used within the eye from which the crystalline lens has been removed, in one of three positions: between the back surface of the cornea and the front surface of the iris and centered in front of the pupil, the anterior chamber lens; in the plane of the pupil, the iris plane lens; and just behind the iris and centered with respect to the pupil, the posterior chamber lens. This invention is concerned with the posterior chamber lens only.

PRIOR ART

Posterior chamber intraocular lenses are made of homogeneous transparent plastic and also of glass, with plastic used primarily. With one exception, the posterior chamber lenses of the prior art have two convex spherical surfaces, or one convex spherical and one plane surface, the exception being a posterior chamber lens produced by Optical Radiation Corporation in which lens the anterior convex surface decreases in curvature from its apex to its periphery.

The novel aspheric intraocular lens of this invention is a posterior chamber lens with at least one convex aspheric surface of revolution with an apical umbilical point at which the derivative of curvature vanishes and which lens surface is designed to have a continuously and regularly increasing refractive power from its apex peripheralward in its optically active area and which lens surface also increases continuously and regularly in curvature from its apex peripheralward in its optically active area. The opposite surface may be plane, convex, concave, convex spherical, concave spherical, or a second convex aspheric surface of revolution, which surface also increases in curvature along a meridian from its apex to its periphery.

The novel lens of this invention is designed to have continuously, regularly, and progressively increasing refractive power from its axis peripheralward in its optically active area, and to achieve the following results: the correction of the axial refractive error of the aphakic eye in which it is placed, and the production of clear central vision over a continuous range of distances from far to near, where far is defined as six meters and beyond and near or reading distance is defined as generally about 40 cm from the eye, but may be as close as 33 cm. This last unique function of the novel intraocular lens of this invention which simulates the physiologic accommodation of the phakic eye will hereinafter be termed accommodation.

IN THE DRAWINGS

FIG. 1 is a schematic drawing of a meridian section, drawn to scale, of the basic optical elements of the model aphakic eye used in this invention;

FIG. 2 is a schematic drawing of a meridian section, drawn to scale, of the optical system of the model aphakic eye with the novel aspheric intraocular lens of this invention in a centered position in the posterior chamber of the eye;

FIG. 5 is a graph of the length of the ideal model aphakic eye from the apex of the cornea to the inner surface of the sclera along its geometrical axis versus the apical radius of curvature of the front surface of the cornea;

FIG. 6 is a schematic representation of a cross-section of a cone-shaped beam of light within which is outlined a cone-wedge of light;

Figure 3:
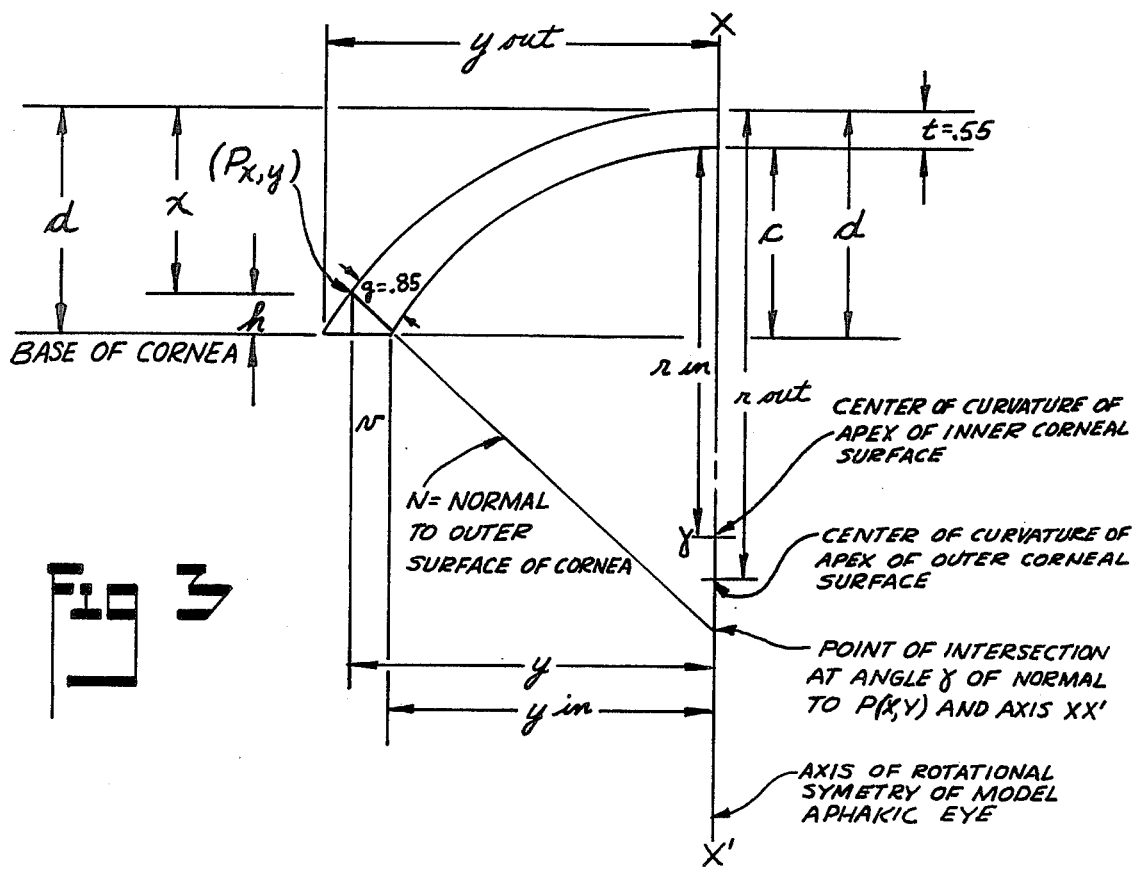
FIG. 3 is a schematic drawing of a partial meridian section, drawn to scale, showing the relationship of the outer and inner surfaces of the cornea of the model aphakic eye.

FIGS. 7a and 7b, not drawn to scale, together illustrate the two main functions of the novel aspheric intraocular lens of this invention; the correction of the axial refractive error of the aphakic eye for distant vision, and the providing of accommodation in said eye for near vision; and FIGS. 8a through f, drawn to scale, show meridian sections of the various embodiments of the novel aspheric intraocular lens of this invention.

MODEL APHAKIC EYE

For use in designing the novel posterior chamber aspheric intraocular lens of this invention, hereinafter defined simply as the novel lens, I have designed and utilized an idealized geometrical mathematically-definable model aphakic eye which is rotationally symmetrical about an anterior-posterior axis, said axis being the optical axis of the model aphakic eye as well as the anterior-posterior or geometrical axis, which axis intersects the anterior corneal apex and the posterior external sclera of the model aphakic eye at the anterior and posterior poles respectively. That portion of the optical axis between the anterior pole and the front surface of the retina is the internal anterior-posterior axis.

Within the retina and about 0.20 mm behind the front surface of the retina is the layer or rods and cones, the light sensitive layer of about 0.04 mm thickness which in turn lies in front of and is concentric with the inner surface of the sclera by about 0.26 mm. Thus the front surface of the layer of rods and cones of the retina lies within the retina and concentric with and separated from the scleral inner surface by a distance of about 0.30 mm and is at a distance from the anterior pole of the model eye equal to the length of the internal anterior-posterior axis plus 0.20 mm, the 0.20 mm representing the distance from the anterior surface of the retina to the anterior surface of the layer or rods and cones.

In the model aphakic eye, for the purpose of this invention, both the convex anterior and the concave posterior surfaces of the cornea are end-sections of prolate ellipsoids of revolution whose major axes are coaxial with the geometrical axis of the eye. At its apex, the thickness of the cornea of the model eye is 0.55 mm and at its periphery the thickness of the cornea is 0.85 mm. The thickness of the sclera is about 0.66 mm.

The sclera of the model aphakic eye joins the cornea at its base at coaxial and coplanar inner and outer sclero-corneal junctions. The scleral cavity of the model aphakic eye is spherical with its center of curvature on the optical axis of the model eye. The inner surface of the sclera joins the inner surface of the cornea in a protruding cusp-like coaxial circle and extending inwardly from said circle is the iris, which terminates in a circular coaxial aperture, the pupil of the eye. The distance from the apex of the concave corneal inner surface to the base of the cornea at the plane of the back surface of the iris is 3.05 mm, while the distance from the apex of the outer surface of the cornea to the base of the cornea is 3.6 mm.

The usual range of radii of curvature of the apex of the anterior surface of the human cornea extends from 6.80 mm to 8.80 mm with the majority of values lying between 7.20 mm and 8.10 mm. The anterior surface of the human adult cornea with an apical radius of curvature less than 6.80 mm or greater than 8.80 mm is seldom seen and often is pathological, as in keratoconus and buphthalmos respectively. I have used as the radii of curvature at the apex of the anterior surface of the cornea values from 6.80 mm to 8.80 mm for the model aphakic eye used in this invention and have used as the corresponding radii of curvature at the apex of the posterior surface of the cornea of the model eye values from 5.6667 mm to 7.3333 mm.

Throughout this specification I have used for the model aphakic eye the following values for the indicts of refraction of the cornea, aqueous humor, and vitreous humor respectively; 1.3763, 1.336, and 1.336, and I have assumed that the index refraction of the retina is the same as that of the vitreous humor, 1.336. Measurement of the length of the eye by ultrasound encompasses the distance from the apex of the cornea to the internal limiting membrane of the retina which is an extremely thin layer of unknown index of refraction. The index of refraction of that portion of the retina between the internal limiting membrane and the layer of rods and cones, 0.2 mm in thickness, is likewise not known, and for the purpose of the model aphakic eye I have assumed that it be 1.336. For the purpose of this specification, the novel intraocular lens will be made of polymethylmethacrylate of $n=1.491$. Polymethylmethacrylate is the most commonly used material for intraocular lenses; other materials, such as glass, for example, and plastics of indices of refraction differing from that of polymethylmethacrylate may also be used. Plastic and glass of various filter quanties may also be used. The novel lens of this invention is thus not limited to one particular homogeneous transparent optical media but may be designed with any of the present optical materials used for intraocular lenses and other materials which may be available in the future.

The basic optical elements of the model aphakic eye which have been described are shown schematically in FIG. 1, drawn to scale, which is a meridian section. FIG. 2, drawn to scale, is a meridian section through the optical system of the model eye with the novel lens in a centered position in the posterior chamber of the eye. The optical system of the model eye with the novel lens in place as depicted in FIG. 2 consists of three consecutive contacting aspheric lenses on a common optical axis of rotational symmetry, the first of said lenses being the cornea where the index of refraction $n=1.3763$, with its convex aspheric surface in contact with air, $n=1.00$, and its concave aspheric posterior surface in contact with the front surface of an aqueous humor aspheric lens where $n=1.336$, the back surface of the relatively thick aqeous humor lens being in contact through the pupil with the anterior surface of the novel lens, the third of said lenses where, for the purpose of illustration, $n=1.491$, the back surface of the novel lens being in contact with the vitreous humor where $n=1.336$. Note that the diameter of the implanted novel lens in the model aphakic eye is about 6 mm, well in excess of the diameter of the pupil which is generally about 3.5 mm. Hence, the periphery of the novel lens beyond a diameter of about 4.5 mm is not optically active but is simply a carrier portion of said novel lens. When, in the specification, I speak of a surface of the novel lens increasing in curvature and refractive power peripheralward, it is to be understood that it is only the optically active portion of the lens behind the pupil which is being considered and that the non-optically active portion of the lens surface may in fact not increase and may even decrease in curvature and refractive power.

All prior art posterior chamber intraocular lenses are identified by their dioptric power within the eye, for example, 17.00, 17.50, 18.00, 18.50, 19.00, 19.50, 20.00, etc., diopters. In the prior art the dioptric power of the intraocular lens to be used in a given aphakic eye is calculated by means of equations supplied by the manufacturer of the lens. The calculation utilizes two basic measurements of the eye and a hypothetical index of refraction, $n=1.3375$ for the cornea, aqueous humor, and vitreous humor, and an assumed standardized distance of the front surface of the cornea to the front surface of the intraocular lens, the basic measurements being the dioptric power or radius of curvature of the front surface of the cornea as determined by measurement with the keratometer or ophthalmometer, and the length of the eye from the apex of the front surface of the cornea to the retina as measured by means of ultrasound. Said equations are concerned only with the dioptric power of the intraocular lens which when placed coaxially in the posterior chamber of the eye and essentially centered with respect to the pupil and at the assumed standardized distance from the apex of the front surface of the cornea, will cause a parallel bundle of paraxial incident light rays incident upon and refracted by the front surface of the cornea, then passing through the pupil and refracted by the intraocular lens into the vitreous humor, to come to a focus at a distance behind the apex of the front surface of the cornea equal to the length of the eye as measured by ultrasound plus 0.2 mm, taking into consideration the fact that the layer of rods and cones of the retina is at a slightly greater distance, 0.2 mm, from the apex of the cornea.

In all of the prior art methods of calculating the power of the intraocular lens which will be required to correct the refractive error of the postsurgical aphakic eye, a single hypothetical value for the index of refraction of the cornea and aqueous and vitreous humors of said aphakic eye is assumed, the value, as stated, being $n=1.3375$. Using such an assumed value of n for all media, the only refracting surface of the aphakic eye which can be considered in the calculations is the front surface of the cornea. Thus, by the use of the single hypothetical index of refraction for all ocular media of the aphakic eye, the back surface of the cornea is eliminated from calculations and the assumed position of the secondary focus of said single index aphakic eye, i.e., the distance of said secondary focus from the apex of the front surface of the cornea, is simply calculated by means of the paraxial ray equation for a single refracting surface.

Although the use of an appropriate hypothetical index of refraction could yield a correct value for said focal distance, it is incorrect to assume that it is valid to use a single hypothetical value in calculating the required power of the intraocular lens to be implanted in the aphakic eye. In fact, my calculations indicate that a value of 1.3375 for the index of refraction of all ocular medias is a grossly incorrect value when results are compared with calculations wherein the true indices of refraction are used. Unless the cornea is considered as a distinct lens in computations directed at determining the required intraocular lens power for an eye of given length and a cornea of a given apical radius of curvature of its front surface, the lens power determined will be incorrect. Furthermore, it is essential that the cornea be considered as a distinct lens in determining the design of an intraocular lens which both corrects the axial refractive error and provides accommodation.

In the idealized mathematical-geometrical model of the human aphakic eye as shown in FIG. 1, which I have designed for this invention, I have used a prolate ellipsoid of revolution as the outer surface of the cornea of the model aphakic eye whose parameters, apical radius of curvature and eccentricity, define the magnitude and shape of said outer corneal surface. Using the values of t=0.55 mm and q=0.85 mm for the axial and peripheral thicknesses respectively of the cornea of the model aphakic eye, and the value of $e_{out}$=0.50 for the eccentricity of said outer surface, and the ratio of 6/5 for the ratio of the apical radius of curvature of the outer surface of the cornea, $r_{out}$, to that of the inner surface, $r_{in}$, I have programmed a digital computer to determine the eccentricity, $e_{in}$, of the prolate ellipsoid inner corneal surface of the model aphakia eye. As a first example, consider a cornea of said model eye whose radius of curvature of the apex of the outer surface of the cornea, $r_{out}$, is 7.7 mm. The apical radius of curvature of the inner corneal surface, $r_{in}$, is 6.4167 mm as determined by means of said ratio. The distance d from the apex of the outer surface of the cornea of the model aphakic eye to the base of said cornea is 3.6 mm, and the distance c from the apex of the inner surface of said cornea to said base is 3.05 mm. The index of refraction of the cornea of said model eye, $n_{cor}$, = 1.3763 and the index of refraction of both the aqueous and vitreous humors of said model eye, $n_{aq}$ and $n_{vit}$ is 1.336.

FIG. 3, drawn to scale, represents one-half of a meridian section through the cornea of the model aphakic eye, showing the relationship of the outer and inner surfaces of said cornea including its base. A normal N to the outer surface of said cornea which passes through the inner surface of said cornea at its base, forms an angle $\gamma$ with the optical axis XX' of the model aphakic eye. The outer semi-diameter of the cornea, $y_{out}$, is shown at the intersection of the outer corneal surface with the base of said cornea, and the inner semi-diameter, $y_n$, is likewise shown at the intersection of the inner corneal surface with the base of said cornea,. P(x,y) is the point of intersection of said normal with the outer corneal surface at coordinates x,y. The distance q along said normal represents the thickness, 0.85 mm, of the periphery of the cornea of the model aphakic eye. The distance v represents the difference in y values between y and $y_{in}$, h represents the distance d−x. The equation of a conic of prolate type, i.e., which decreases in curvature from its apex peripheralward, including meridian sections of prolate ellipsoids, paraboloids and hyperboloids, is:

$$y = [2rx - (1-e^2)x^2]^{\frac{1}{2}}. \quad\quad 1$$

Using the value $y_{out}$ for y, d for x, $e_{out}$ for e, and $r_{out}$ for r in Equation 1, it becomes:

$$y_{out} = [2r_{out}d - (1-e_{out}^2 d^2)]^{\frac{1}{2}}. \quad\quad 2$$

For the example given, shown in FIG. 3 which is drawn to scale, where $r_{out}$=7.7 mm, d=3.6 mm and $e_{out}$=0.5, $y_{out}$ is calculated by means of Equation 2 to be 6.7614 mm.

Using Equation 1 and the values of $r_{out}$ and $e_{out}$ of this example, a value of x is systematically varied between preselected upper and lower bounds in a binary search by a digital computer, determining with each calculation, a value of y, and using the values of x and calculated y in determining corresponding value of $\gamma$ by means of the following equation:

$$\gamma = \tan^{-1} \frac{y}{r_{out} + (e_{out}^2 - 1)x}, \quad\quad 3$$

and with each calculation within the search, the value of h is determined by means of the following equation:

$$h = d - x, \quad\quad 4$$

and with each calculation within the search, the value of q is determined by means of the following equation:

$$q = \frac{h}{\cos \gamma}. \quad\quad 5$$

When the value of q within the binary search reaches the value of 0.85 mm which is the value of the thickness of the peripheral cornea of the model aphakic eye, representing no more than 15 to 20 values of x within the search, the value of $\gamma$ will have been determined, which in this example is 49.4180°, and h will have been determined, a value of 0.5530 mm.

The value of v is determined by means of the following equation:

$$v = h \tan \gamma, \quad\quad 6$$

and the value obtained is 0.6456 mm.

The value of x within the binary search resulting in the value of q being equal to 0.85 mm is 3.0470 mm, and the value of y is 6.3215 mm. The value of $y_{in}$ is then determined by means of the following equation:

$$y_{in} = y - v, \quad\quad 7$$

and for the example calculation $y_{in}$ is calculated to be 5.6759 mm. The eccentricity of the inner surface of the cornea is then determined by means of the following equation:

$$e_{in} = \left( \frac{y_{in}^2}{c^2} - \frac{2r_{in}}{c} + 1 \right)^{\frac{1}{2}}, \quad\quad 8$$

and the value obtained for this example of the eccentricity of the inner surface of the cornea of the model aphakic eye is 0.5055. The values of $r_{in}$ and $e_{in}$ obtained for this specific example completely define the magnitude and shape of the inner corneal surface of the model aphakic eye of this example while the value of $y_{in}$ defines its lateral extent at the base of the cornea.

The dioptric power $D_{out}$ of the outer surface of the cornea of the model eye at its apex is determined by means of the following equation:

$$D_{out} = \frac{n_{cor} - n_{air}}{r_{out}}, \qquad 9$$

and the value obtained for this example is 48.8701 diopters.

The dioptric power $D_{in}$ of the inner surface of the cornea of the model eye at its apex is determined by means of the following equation $$D_{in} = \frac{n_{air} - n_{cor}}{r_{in}}, \qquad 10$$

and the value obtained for this example is $-58.6439$ diopters. A parallel bundle of paraxial light rays incident upon the front surface of the cornea is refracted by said front surface toward a point behind the corena at a distance $i_{out}$ from the apex of said cornea determined by means of the following equation:

$$i_{out} = \frac{n_{cor}}{D_{out}}, \qquad 11$$

and the value obtained is 28.1623 mm. Said point is 28.1623−0.55 mm or 27.6123 mm behind the apex of the inner surface of the cornea.

The effective power, $D_{cor\text{-}effective}$, of the apex of the front surface of the cornea of the model eye at the apex of the back surface of said cornea is calculated by means of the following equation:

$$D_{cor\text{-}effective} = \frac{n_{cor}}{i_{out} - t}, \qquad 12$$

where t is the thickness of the cornea at the optical axis, and the value obtained for this example is 49.8436 diopters. With the value obtained previously for the power of the inner surface of the cornea of the model eye at its apex, $-58.6439$ diopters, and the value obtained for the effective power of the apex of the front surface of the cornea at the apex of the back surface of said cornea, 49.8436 diopters, the resultant back vertex power of the cornea, $D_{cor}$, of the model eye of this example is obtained by means of the following equation, $$D_{cor} = D_{cor\text{-}effective} + D_{in}, \qquad 13$$

and the value obtained for $D_{cor}$ is $-8.8006$ diopters.

The power at the apex of the aqueous humor lens of the model eye, $D_{aq}$, having the same radius of curvature, $r_{aq}$, as the back surface of the cornea of the model eye, is determined by means of the following equation:

$$D_{aq} = \frac{n_{aq} - n_{air}}{r_{aq}}, \qquad 14$$

and the value obtained is 52.3636 diopters.

Adding the minus back vertex power of the corneal lens of the model aphakic eye to the positive vertex power of the aqueous humor lens surface of said eye, the resultant power, $D_{eye}$, is obtained:

$$D_{eye} = D_{cor} + D_{aq} \qquad 15$$

and the value obtained is 43.5630 diopters.

The converging homocentric bundle of light rays within the aqueous and vitreous humors of the model eye is directed toward a focus at a distance $i_{aq}$ behind the apex of the aqueous humor lens surface, $i_{aq}$ being determined by means of the following equation:

$$i_{aq} = \frac{n_{aq}}{D_{eye}}, \qquad 16$$

and the value obtained is 30.6682 mm.

The distance f of said focus behind the apex of the front surface of the cornea of the model eye is determined by means of the following equation:

$$f = i_{aq} = t, \qquad 17$$

and the value obtained is 31.2181 mm.

Thus, by means of the calculations using Equations 1 through 17, the optical system of the model aphakic eye can be completely specified for any given apical radius of curvature of the outer surface of the corneal lens of said model eye. The same sequence of calculations as just descrited in the example calculation was programmed for a digital computer and computations were done for a series of model aphakic eyes whose apical radii of curvature of the outer corneal surface ranged from 6.80 mm to 8.80 mm in steps of 0.1 mm.

In Table 1, I have listed for the front surface of the cornea of the mcdel aphakic eye, the apical radius of curvature, $r_{out}$; eccentricity, $e_{out}$; dioptric power, $D_{out}$; and the effective dioptric power, $D_{cor\text{-}effective}$, at the vertex of the back surface of the cornea; and have also listed the corresponding apical radius of curvature, $r_{in}$; eccentricity, $e_{in}$; dioptric power, $D_{in}$; and the back vertex power of the corneal lens, $D_{cor}$, for a series of corneas having apical radii of curvature ranging from 6.80 mm to 8.80 mm in steps of 0.1 mm. Also included in Table 1 is the corresponding dioptric power, $D_{aq}$, of the aqueous humor lens surface which has the same apical radius of curvature and eccentricity as that of the back surface of the corneal lens, and the resultant dioptric power, $D_{eye}$, at the apex of the aqueous humor lens surface when the back vertex power of the cornea is combined with the dioptric power of the aqueous humor lens surface, and the back focus, $i_{aq}$, of a paraxial bundle of parallel light rays incident upon the cornea, as measured from the apex of the aqueous humor lens surface and also as measured from the apex of the front surface of the cornea, $i_{aq}+t$, which is listed under f.

In the present state of the art a single hypothetical index of refraction, $n=1.3375$, is used for the aphakic eye in computations directed at determining the required dioptric per of the intraocular lens for the correction of the refractive error of said aphakic eye. In the calculaticns for the data presented in Table 1, the true indices of refraction were used rather than a single hypothetical value for the index of refraction of the eye. Note in Table 1 that the model aphakic eye having a 7.7 mm apical radius of curvature of the front surface of the cornea causes a paraxial bundle of incident parallel light rays to be directed toward a focus 31.2181 mm behind the apex of the front surface of the cornea. Using a single hypothetical value of 1.3375 for the index of refraction of the aphakic eye having the apical radius of curvature of 7.7 mm, the secondary focus of said aphakic eye would be 30.5148 mm rather than 31.2181 mm, an error of 0.7033 mm. In order that said aphakic eye with a single hypothetical index of refraction have a secondary focus of 31.2181 mm, said hypothetical index of refraction would have to be 1.3274.

The model aphakic eye of this invention (see FIG. 1) can be divided geometrically into two portions: an anterior segment which consists of the aspheric corneal lens, the aqueous humor whose front surface matches the aspheric back surface of the corneal lens, and the iris with its coaxial pupil, the plane of the posterior surface of the iris coinciding with the base of the cornea where the cornea and sclera join; and a posterior segment consisting of the spherical sclera containing the vitreous humor which in the model aphakic eye is in contact with the aqueous humor passing through the pupil, the posterior surface of the vitreous humor being bounded by the spherical inner surface of the retina lying concentrically within the spherical sclera, the radius of curvature of the inner surface of the retina being 0.5 mm less than the radius of curvature of the inner surface of the sclera, with the layer of rods and cones of the retina 0.2 mm external to the inner surface of the retina. The axis of rotational symmetry of the model aphakic eye coincides with the corneal axis. Since the aqueous humor and the vitreous humor have the same index of refraction the interface between them does not affect the regularity of light transmission.

For any given anterior segment of the model aphakic eye, the radius of curvature of the spherical scleral cavity, $r_{sclera}$, may vary in magnitude within limits. It has been previously established that the average normal human emmetropic eye has an apical radius of curvature of the anterior surface of the cornea of about 7.7 mm, that the average normal axial length of said eye from the corneal apex to the inner surface of the sclera is about 24.25 mm and that when an intraocular lens is implanted in said eye, its power is about 19 diopters to achieve emmetropia. In my calculations with respect the model aphakic eye, using the actual indices of refraction of the ocular medias and that of the included intraocular lens, I have determined that the model aphakic eye with a 7.7 mm apical radius of curvature of the anterior surface of the cornea and with an incorporated intraocular novel lens of this invertion 1 mm thick and having a back vertex power of 19.00 diopters, emmetropia is achieved when the length of the eye from the apex of said cornea to the inner surface of the sclera along the axis of said eye is 24.1247 mm, with the radius of curvature of the scleral cavity 11.0472 mm. In said eye, the ratio of the radius of curvature of the scleral cavity with respect to said apical radius of curvature of the anterior surface of the cornea is $r_{sclera}/r_{cornea}$ and for the example used is 11.0472/7.7 or 1.4347.

Figure 4:
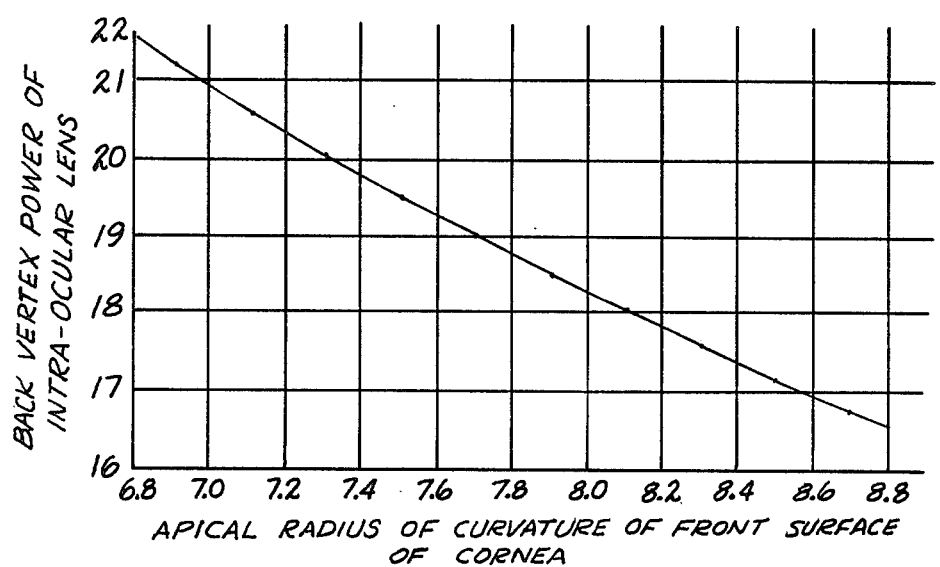
FIG. 4 is a graph of the back vertex power of the novel intraocular lens of this invention versus the apical radius of curvature of the anterior surface of the cornea of the ideal model aphakic eye, for the condition of emmetropia.

If it is assumed that the ratio 1.4347 for $r_{sclera}/r_{cornea}$ is the ideal ratio for the model aphakic eye for the normal range of apical radii of curvature of the anterior surface of the cornea of the model aphakic eye, then the back vertex power of the incorporated novel intraocular lens required for producing emmetropia in said ideal model aphakic eye must vary in accordance with the apical radius of curvature of the anterior surface of its cornea. FIG. 4 shows graphically, for the normal range of apical radii of curvature of the anterior surface of the cornea, the back vertex power of the incorporated novel intraocular lens versus the apical radius of curvature of the front surface of the cornea of the ideal model aphakic eye for the condition of emmetropia.

FIG. 5 shows graphically for the ideal model aphakic eye, the length of the eye from the apex of the front surface of the cornea to the inner surface of the sclera along the geometrical axis of the ideal model aphakic eye versus the apical radius of curvature of the front surface of the cornea of the ideal model aphakic eye. Should the model aphakic eye be other than the ideal such that the ratio $r_{sclera}/r_{cornea}$ be greater than 1.4347, i.e., the length of the eye is relatively long with respect to the apical radius of curvature of the front surface of the cornea, then the back vertex power of the included intraocular lens required for emmetropia would be less than that for emmetropia in the ideal model aphakic eye having the same apical radius of curvature of the front surface of the cornea. Should said ratio be less than 1.4347, then the back vertex power of the included intraocular lens required for etmetropia would be greater than that required for emmetropia in the ideal model aphakic eye having the same apical radius of curvature of the front surface of the cornea.

It is generally thought and stated that an increase or decrease in the length of the eye by one-third mm corresponds to change in the refractive status of the eye by one diopter. Such an estimate should not be relied upon as it can result in considerable error in the power of the intraocular lens required to correct the refractive error of the aphakic eye. In my research, I have determired (see FIG. 4) that the back vertex power of the intraocular lens required for the correction of the refractive error of the ideal model aphakic eye varies considerably as the apical radius of curvature of the anterior surface of the cornea in said ideal model aphakic eye ranges from 6.8 mm to 8.8 mm. I have also determined that for a model aphakic eye of a given apical radius of curvature of the front surface of the cornea, there is considerable variation in the rate of increase or decrease per unit change in eye length, of the back vertex power of the incorporated intraocular lens required to produce emmetropia, i.e., as the ratio of $r_{sclera}/r_{cornea}$ varies. For example, in the model aphakic eye of 7.7 mm apical radius of curvature of the front surface of the cornea and an included intraocular lens of 19.00 diopters back vertex power, emmetropia prevails when the length of the eye from the corneal apex to the inner surface of the sclera along the axis of the eye is 24.1247 mm. If the length of the eye is 24.4130 mm (0.2883 mm longer) emmetropia prevails if the back vertex power of the intraocular lens is 18 diopters. If the length of the eye is 23.8449 mm (0.2798 mm shorter) emmetropia prevails when back vertex power of the included intraocular lens is 20 diopters. When the length of the eye from the corneal apex to the inner surface of the sclera along axis of the eye is 22.8026 mm, an increase in length by 0.2497 mm results in a change of one diopter in the required back vertex power of the intraocular lens to correct the ammetropia (a back vertex power from 24.00 diopters to 23.00 diopters). When the length of the eye is 25.6575 mm a decrease in length of the eye of 0.3258 mm results in a change of one diopter in the required back vertex power of the intraocular lens to correct the ammetropia (from a back vertex power of 14.00 diopters to 15.00 diopters). Thus the back vertex dioptric power required of the intraocular lens for the correction of the ammetropia of the model aakic eye is non-linear with respect to eye length and the change in dioptric power of the intraocular lens required for various amounts of ammetropia in an eye with a given apical radius of curvature of the front surface of the cornea differs considerably for the eye which is relatively short as compared to the eye which is relatively long.

In the model aphakic eye with a 6.8 mm apical radius of curvature of the front surface of the cornea the rate of change of back vertex power of the incorporated intraocular lens can be as high as 5 diopters per mm of change in eye length. In the model aphakic eye with an 8.8 mm apical radius of curvature of the front surface of the cornea the rate of change of back vertex power of the incorporated intraocular lens may be as low as 2 diopters per mm of change in eye length.

In view of the complexity of the factors involved in formulas in the present state of the art for calculating the required dioptric power of an intraocular lens to correct the refractive error of the aphakic eye, factors such as the use of a hypothetical single index of refraction thereby eliminating the cornea as a lens and resulting in erroneous values for calculated lengths of the eye, and erroneous calculated values for the required dioptric power of the intraocular lens, I have determined that the proper way to calculate the required back vertex power of the novel intraocular lens is to use paraxial ray equations with the actual indicies of refraction of the optical medias of the model aphakic eye in conjunction with the novel lens and its index of refraction, calculations which I have programmed for and which have been performed by a digital computer. The calculations are performed serially for corneas having apical radii of curvature of the front surface of the cornea, $r_{out}$, within the range of from 6.8 mm to 8.8 mm in steps of 0.1 mm, and for each of said apical radii of curvature in the series, computations were made for a range of eye lengths, $l_{ultra}$, the length as measured by ultrasound, and $l_{rodcone}$, the length of the eye to the layer or rods and cones of the retina, such that the back vertex power of the novel lenses in the series for each value of $l_{rodcone}$, fell at one-half diopter intervals for values of $l_{rodcone}$ ranging from 20 mm to 30 mm, the smaller values of $l_{rodcond}$ being associated with the smaller values of $r_{out}$ and the larger values of $l_{rodcone}$ being associated with the larger values of $r_{out}$. It is to be noted that when a novel lens of this invention is ordered for an aphakic eye, the length of the eye, $l_{ultra}$, is supplied with the order, but that the lens supplied is calculated for $l_{rodcone}$; $l_{rodcond}$ being 0.2 mm longer than $l_{ultra}$.

In addition to the determination of the required back vertex power of the novel lens to produce emmetropia in the model aphakic eye, non-paraxial ray equations were programmed for the digital computer and computations were performed to determine the design of the novel intraocular lens for the production of accommodation over the entire range of apical radii of curvature and associated eye lengths of the model aphakic eye which itself is representative of the actual human aphakic eye. The doctor need only supply to the manufacturer or to the medical supplier who maintains an inventory of the novel lens, the apical radius of curvature, $r_{out}$, of the front surface of the cornea and the length, $l_{ultra}$ of the eye in which the lens is to be placed, and a specific lens identified by r and l values closest to those supplied by the doctor, will be selected from inventory, packaged and labled with the selected r and l values and back vertex power, and provided to the doctor. As an example the valve supplied by the doctor for r could be 7.71 mm and the value supplied for l could be 23.60 mm. The lens supplied to the doctor would be labled, r=7.70 mm, l=23.62, BVP (back vertex power)=19.00 D. There is no need for the doctor to calculate a back vertex power for the intraocular lens, although he may do so if he desires, as the design of the lens and its back vertex power are specific for the r and l values of the supplied lens. Thus by means of predetermined calculations using the true indices of refraction for each ocular media the design and power of the lens required for the desired correction of the axial refractive error and for the providing of the desired amount of accommodation has been accomplished using only the two parameters supplied by the doctor, r and l.

In actual practice the lens series is divided into a range or series of subsets of lenses, each subset corresponding to and being identified by a given $r_{out}$ and consisting of a series of lenses, each lens within the subset identified by the given $r_{out}$ and also with each $l_{ultra}$, and each BVP, as found within the range of $l_{ultra}$ values of said subset. Physically the lenses of a given subset may be stored sequentially according to the $l_{ultra}$ value in a cabinet consisting of a vertical column of drawers identified by the parameter $r_{out}$, with each drawer in the column identified by both the $r_{out}$ value and the appropriate $l_{ultra}$ and BVP values within the sequence of $l_{ultra}$ values within the subset.

The value of the lens series to the doctor lies in the fact that the range of apical radii of curvature of the front surface of the cornea, $r_{out}$, is divided into many closely spaced values as is the range of eye lengths, $l_{ultra}$. This allows for the stocking as inventory many lenses whose parameters are extremely close to those parameters supplied by the physician ordering a lens with specific parameters of $r_{out}$ and $l_{ultra}$. In Table 2 I have tabulated the values of several subsets of the lens series of this invention in an orderly position within the domain of $r_{out}$ and $l_{ultra}$ values. Within a subset of lenses for a given $r_{out}$, the values of $l_{ultra}$ differ sequentially by an amount representing 0.50 diopter intervals of the back vertex power of the novel lens. The middle value of the subset is that value calculated for the ideal model aphakic eye wherein the ratio $r_{sclera}/r_{cornea}=1.4347$. The remainder of the values of $l_{ultra}$, 12 above and 12 below said middle value of $l_{ultra}$, represents those lenses for model aphakic eyes shorter and longer than the ideal, the total range of back vertex power in a subset being 12 diopters. The number of lenses within the series is 525. The specificity of the novel lens may be increased by increasing the number of lenses in the series, by increasing the number of $r_{out}$ values between 6.8 mm and 8.8 mm and by reducing the back vertex power interval of the novel lenses in the subset from 0.50 diopters to 0.25 diopters. Since the accuracy of the determination of $r_{out}$ with the keratometer or ophthalmometer is limited, and since the measurement of $l_{ultra}$ with ultrasound also has limitations in accuracy, an increase in the number of lenses within the domain of the series may be unwarranted.

ACCOMMODATION

The term accommodation as used in this specification implies that the novel intraocular lens of this invention when utilized in the posterior chamber of the human eye provides clear central vision for distance and at all intermediate distances from far to usual reading distance of about 40 cm or slightly closer. Since the novel lens is fixed in shape, such accommodation is provided by the optical properties of the lens rather than a changing lens shape as in the normal physiologic accommodation of the human crystalline lens.

As I stated earlier, the novel intraocular lens of this invention is designed to have a continuously, regularly, and progressively increasing refractive power from its axis peripheral ward in its optically active portion. In my research utilizing the model aphakic eye in conjunction with ray trace equations programmed for a digital computer, I have determined that the required increasing refractive power for accommodation can be achieved in the novel lens of this invention with each of the following lens designs:

1. the front convex surface of the novel lens increasing continuously ard regularly in curvature and refractive power from its axis peripheralward and the back surface plane,
2. the front convex surface of the novel lens increasing continuously and regularly in curvature and refractive power from its axis peripheralward and the back surface convex spherical,
3. both the front and the back convex surfaces of the novel lens increasing continuously and regularly in curvature and refractive power from its axis peripheralward,
4. the back convex surface of the novel lens increasing continuously and regularly in curvature and refractive power from its axis peripheralward and the front surface plane,
5. the back convex surface of the novel lens increasing continuously and regularly in curvature and refractive power from its axis peripheralward and the front convex surface spherical.
6. the front convex surface of the novel lens increasing continuously and regularly in curvature and refractive power from its axis peripheralward and the back surface concave spherical.

All of the above described embodiments of this invention have the quality of increasing refractive power peripheralward and can provide clear distance vision and accommodation when implanted in the posterior chamber of the aphakic eye. Each embodiment, however, differs somewhat in its optical properties such as the amount of astigmatism associated with the accommodating function and the effect upon peripheral vision. Based upon computed ray trace results, that embodiment wherein the front surface of the novel lens is convex spherical and the back surface is convex aspheric increasing continuously and regularly in curvature and refractive power from its axis peripheralward, is the preferred embodiment.

Some practical considerations may influence the use of one design in preference to another. For example, the use of one plane surface (rather than two curved surfaces) in combination with the aspheric surface of revolution of increasing curvature and refractive power peripheralward would facilitate production of the novel lens of this invention and thus reduce its cost. The use of a flat or concave back surface of the lens reduces potential damage to the lens when using a laser in eliminating membrane formation or opacification behind the implanted lens. Based upon the above two considerations, an alternative to the preferred embodiment of the novel lens of this invention would utilize a positive aspheric surface of revolution which increases in curvature and refractive power peripheralward as the front surface and would utilize a plane or concave back surface.

THEORETICAL BASIS FOR ACCOMMODATION

Consider now the refraction by the model aphakic eye of this invention of an incident bundle of parallel light rays whose chief ray coincides with the optical axis of said model eye. The pupil of the model aphakic eye concentric to the optical axis of the eye and approximately 3.5 mm in diameter, limits the extent of said incident bundle of light rays to be considered.

It is known that an cptical surface is aplanatic for an incident bundle of coaxial parallel light rays when the surface is the end of a prolate ellipsoid whose eccentricity is the ratio of the index of refraction of the incident media divided by the index of refraction of the second media. For the outer surface of the cornea as a refracting surface bounding the corneal media, the eccentricity required for aplanaticism would be 1/1.3763 or 0.7266. An even higher eccentricity of the front surface of the cornea is required when both surfaces of the cornea are taken into account. The eccentricity of the outer convex surface of the cornea of the model aphakic eye is only 0.50 while that of the inner concave surface of said cornea is close to 0.50, ranging from 0.467 to 0.547, and in the example used previously in the specification, eccentricity is 0.5055. The net effect of refraction of said bundle of light rays through the corneal lens of the model aphakic eye into the aqueous and vitreous humors is only a small amount of residual spherical aberration. It is the novel intraocular lens of this invention, by virtue of its considerable increasing refractive power from its apex peripheralward, which provides the required increasing refractive power to the optical system of the model eye necessary for accommodation as this term is defined hereinabove.

A point source of light emits light energy equally in all directions. The luminous flux from said point source to a relatively small circular aperture concentric to a light ray from said source and at a relatively large distance from said point source, may be considered to be uniformly distributed throughout the area of the aperture. A point source of light at approximately 40 cm from the eye having a pupil of 4 mm or less may be ccnsidered as this point source of light. The light energy emitted by and diverging from the point source to the aperture is in the form of a cone. At the aperture an optical system may act upon said cone of light and cause it to converge. In FIG. 6, I have depicted schematically such a cone-shaped diverging beam or cone of light bounded by the border of a circular aperture. Within the cone of light, I have drawn two pairs of interrupted lines originating at the point source of light. The outer lines of each pair represents elements of an outer cone and the inner lines of each pair represents elements of an inner cone. I have defined those light rays emanating from said point source and lying between said outer and inner cones as a cone-wedge of light. At the aperture which defines the base of the cone of light, the outer cone of the cone-wedge of light has a diameter $s_{out}$ and the inner cone of the cone-wedge of light has a diameter $s_{in}$. The distance $$\frac{s_{out} - s_{in}}{2}$$

is the cross-sectional width of said cone-wedge of light. The average diameter, b, of the cone-wedge of light is given by the following equation:

$$b = \frac{s_{out} + s_{in}}{2} \qquad 18$$

It is necessary at this point to define what is meant by focus. Since the novel lens of this invention increases in refractive power continuously, regularly, and at a progressively increasing rate along a meridian from its apex peripheralward, there can be no geometrical point focus for an axial object point source of light for any given coaxial zone of the optical system of the model aphakic eye containing the novel lens but rather a focus which consists of a minimal cross-sectional area centered about the optical axis representing the greatest concentration of light rays or luminous flux from said coaxial zone. For a homocentric bundle of incident parallel light rays surrounding the optical axis of the model aphakic eye, refracted by the cornea and aqueous humor and passing through the pupil of about 3.5 mm in diameter and refracted by the novel lens, those refracted rays emitted from the posterior surface of the novel lens from a central area about 1.5 mm in diameter are converged toward a minimal cross-sectional area centered about the optical axis which area is about the size of the inner end of a single retinal receptor of about 0.002 mm diameter. It is the 0.002 mm diameter of the retinal receptor area which is the unit receptor area which limits the size of the central area of the back surface or the novel lens which can contribute light only to said unit receptor area and also limits, for a point source of light at an intermediate or near axial object distance, the width of the cross-section of a cone-wedge of light at the back surface of the novel lens which can contribute light to said unit receptor area, said width being approximately ¾ mm centrally and decreasing peripheralward.

For the model aphakic eye with the novel lens implanted, the eye can be said to be in focus for a given axial object distance when the maximum luminous flux from an axial object point source of light at said distance is focused upon said unit receptor area at the rod and cone layer of the retina. When said axial point source of light is distant, i.e. beyond 6 meters, and the eye is in focus for said distance, the eye is said to be emmetropil. As I have already indicated, it is only the light emitted from the central 1.5 mm diameter area of the back surface of the novel lens which is directed toward the unit receptor area at the layer of rods and cones in the condition of emmetropia. The remainder of the refracted light rays from said incident bundle of homocentric parallel rays emitted from the back surface of the novel lens are not in focus and are widely distributed to a great number of retinal receptors surrounding said unit receptor area at the optical axis of the eye. The net effect is an intense sharply focused image at the layer of rods and cones, the size of a unit receptor area, of the distant axial point source of light, surrounded by a low level background illumination. If the homocentric bundle of light rays incident upon the cornea of said emmotropic eye diverge from an axial object point source of light at a relatively close distance from the model eye containing the novel lens, a distance of 40 cemtimeters, for example, the paraxial conjugate focus of said axial object point source of light will be behind the layer of rods and cones of the retina. The central area of the back surface of the novel lens contributing light to a single unit receptor area at the layer of rods and cones will be markedly reduced in extent or practically eliminated. Instead, light from a coaxial annular zone on the back surface of the novel lens, i.e., a cone-wedge of light, will be sharply focused upon said unit receptor area at the layer of rods and cones. Stated in another way, said near axial object point source of light and the unit receptor area at the layer of rods and cones, are conjugate through said coaxial zone and cone-wedge of light. The remainder of the light emitted from the back surface of the novel lens is not in focus and is widely distributed over the surrounding retina. The net effect is an intense sharply focused image at the layer of rods and cones, the size of a unit receptor area, of the near axial point source of light, surrounded by a low level background illumination.

The above description of refraction of a cone-wedge of light is that for a single axial point source of light at a relatively close distance, i.e. approximately 40 cm, from said model eye made emmetropic by the novel lens of this invention. For many off-axis point sources of light originating in a plane perpendicular to the optical axis of the said emmetropic eye and containing said relatively close axial point source of light, refraction by said emmetropic eye of cone-wedges of light from each of said off-axis points proceeds in an essentially similar manner to that of the single axial point source of light, the slight difference being that each such off-axis cone-wedge of light is slightly out of round where it enters the cornea and the zone of the cornea upor which the cone-wedge of light is incident is displaced slightly in the direction of the off-axis point source of light. The plane of the many point sources of light constitutes an object plane and the point sources of light may be of various intensities and may together comprise a variety of formed patterns, becoming visual targets for said model aphakic eye containing and made emmetropic by the novel lens of this invention. The axial portion ofthe model aphakic eye including the axial portion of the contained novel lens of this invention which corrects the axial refractive error, i.e., the ocular media along and adjacent to the optical axis, subserves clear, straight ahead distance vision; while the near-by circular or near circular zones of the ocular media, as a result of the increasing refractive power peripheralward of the novel intraocular lens of this invention, refract cone-wedges of light from many point sources of light in a given intermediate or near object plane, subserving clear near vision for the given intermediate or near object plane. For an axial point source of light and likewise for each point source of light in the object plane containing said axial point source of light, the average diameter of the cone-wedge of light at the anterior corneal surface of the model eye, is a function of both the aspheric novel lens and the object plane distance, the greater the object plane distance, the smaller the average diameter, b, of said cone-wedge of light; and the more rapidly the novel lens increases in power peripheralward, the smaller the average diameter. The diameter of the outer border of a cone-wedge of incident light at the outer surface of the cornea, subserving near vision, generally does not exceed 3.8 mm, approximately the diameter of the entrance pupil of the model aphakic eye, the entrance pupil being the slightly enlarged image of the actual pupil as produced by the aqueous humor and the corneal lens, with respect to the object plane distance.

FIGS. 7a and 7b are drawings of meridian sections of identical model eyes containing identical novel lenses, which drawings together schematically represent the two functions of the novel lens of this invention; the correction of the axial refractive error of the aphakic eye for distance vision; and the providing of accommodation in said aphakic eye for near vision.

In FIG. 7a a homocentric bundle of parallel light rays, including an axial ray, is incident upon the cornea and is refracted by the corneal lens, the aqueous humor lens to pass through the pupil and then refracted by the novel lens. Centered within said homocentric bundle of parallel light rays, are those rays, which after said refractions, emerge from the central area of the back surface of the novel lens, an area having a diameter of about 1.5 mm, as a converging bundle of light rays proceeding toward the retina. It is this portion of the converging refracted beam of light which, at the layer of rods and cones of the retina, has a minimal cross-sectional area the size of a unit receptor area, about 0.002 mm in diameter. The remainder of the incident and refracted light beam surrounding said central converging portion is widely distributed to many surrounding retinal receptors so that only a very small amount of light is received by each of said surrounding receptors. FIG. 7a represents the condition of emmetropia with clear distance vision in the model aphakic eye containing the novel lens of this invention.

In FIG. 7b a homocentric bundle of diverging light rays from a near axial point source of light is incident upon the cornea and is refracted by the corneal lens, the aqueous humor lens to pass through the pupil and then refracted by the novel lens. Included in said homocentric bundle of diverging light rays incident upon the cornea, is a peripheral cone-wedge of light which, after said refractions, proceeds as a converging cone-wedge of light from the back surface of the novel lens, toward the retina. It is the converging cone-wedge of light which, at the layer of rods and cones of the retina, has a minimal cross-sectional area, about 0.002 mm in diameter, heretofore referred to as the unit receptor area. The remainder of the incident cone of light other than that represented by the converging cone-wedge of light, after refraction by the novel lens, is directed to points behind the retina and is widely distributed to many surrounding retinal receptors so that only a very small amount of light is received by each of said surrounding receptor areas. FIG. 7b represents accommodation and clear near vision in the model aphakic eye made emmetropic and accommodating by the implanted novel lens of this invention.

MATHEMATICAL DESCRIPTION OF THE ASPHERIC NOVEL LENS SURFACE

The novel lens of this invention is intended to provide clear vision at 40 cm, representing accommodation as previously defined of 2.5 Diopters (i.e. 1 meter divided by 40 cm) which, in the optical field, represents clear vision for the usual or normal reading distance of 16 inches.

Also, in the model aphakic eye and referring to the average diameter b of the cone-wedge of light at the pupil of the eye as hereinabove discussed and depicted in FIG. 6, the novel lens of this invention has a y coordinate for this cone-wedge of light, i.e. distance lateral to the axis of the novel lens, which corresponds to b/2, i.e. about 1.7 mm, for the usual or normal case, such that the corresponding cone-wedge of light emerging from the back surface of the novel lens is focused as this term is defined herein upon the rod and cone layer of the retina and hence the rod and cone layer is conjugate to the object plane at 40 cm from the eye with respect to said cone-wedge of light.

To accomplish the above the design of the novel lens of this invention requires that it increase in power peripheralward to achieve adequate accommodation and that at least one of its surfaces be aspheric with increasing curvature and refractive power peripheralward. It is necessary that the novel lens have minimal change in refractive power centrally to achieve clear distance vision and with increasing distance from the axis of the lens, the rate of increase in refractive power must accelerate to achieve clear intermediate and near vision. Mathematically said aspheric surface of increasing curvature and refractive power peripheralward has its y coordinate at each point along its surface as defined by the following expression:

$$y = (Ax + Bx^2)^{\frac{1}{2}} + Cx^{(p)} + Dx^{(q)} + Ex^{(z)} \qquad 19$$

where $A = 2r_{apex}$, $B = (e^2 - 1)$, where e is the eccentricity at the apex of said surface and where C, D, and E are integral or non-integral coefficients of $x^{(p)}$, $x^{(q)}$, and $x^{(z)}$ respectively, and where p, q, and z can be integral or non-integral exponents of x, and where r ranges from 5 mm to 150 mm, where e ranges from 0.0 to 4.0, where at least one of the values of C, D, and E is other than zero, values of C, D, and E ranging from 0.0 to ±9, the values of p, q, and z range from a value of 0.5 to 6.0, and where the non-bracketed terms of said expression function in combination to modify the first bracketed term which is that of a conic to change the rate at which curvature and refractive power of said conic occur peripheralward in the aspheric surface of the lens.

As a specific example of a novel lens of this invention, consider the model aphakic eye of the following parameters as are heretofore referred to: $r_{out} = 7.7$ mm, $f = 31.2181$. This model aphakic eye, used previously as the first example (see Table 1), required a novel lens of this invention having a back vertex power of 19.00 diopters to correct its power deficiency and result in emmetropia. The incorporated novel intraocular lens in the preferred embodiment has the following parameters: diameter 6 mm, center thickness 1 mm, radius of curvature of front surface 21.3793 mm with a dioptric power of 7.25 diopters, apical radius of curvature of back surface 13.2314 mm with a dioptric power of 11.7146 diopters. The front surface is positive spherical and the back surface is a positive aspheric surface of revolution with an apical umbilical point at which the derivative of curvature vanishes. With the apex of the back surface as origin, and using Cartesian coordinates, the back surface is described in terms of equation 19 and using the actual values for coefficients A, B, C, D, and E, and for exponents p, q and z, equation 19 becomes:

$$y = (26.4628x + 8x^2)^{\frac{1}{2}} - 4.6649x^{1.525} + 7.3709x^{2.3} - 9x^{-5}. \qquad 20$$

The novel lens as described mathematically above represents the preferred embodiment of the novel lens of this invention and within the model aphakic eye for which it is designed it fully corrects the axial refractive error and simultaneously provides clear central vision over a continuous range from distance to near, where near is 40 cm from the model aphakic eye containing said novel lens.

The increase in refractive power of the novel lens peripheralward is accompanied by an invariable associated meridional astigmatism which also increases peripheralward. The effect of said astigmatism is to progressively reduce the effective cross-sectional width of the cone-wedge of light at the back surface of the novel lens as the object plane distance is reduced and the associated average diameter, b, of the cone-wedge of light is increased. However, despite said astigmatism, there is sufficient contrast in the perceived retinal image for good intermediate and near vision.

In FIGS. 8a, 8b, 8c, 8d, 8e and 8f, I have drawn to scale various embodiments, including said preferred embodiments, of the novel intraocular lens of this invention which have at least one of their two surfaces increasing in curvature and refractive power peripheralward such that the novel lens increases in refractive power peripheralward, continuously, regularly and progressively to provide accommodation from far to near in the model aphakic eye.

Using the model aphakic eye of the previous example, i.e., that with the parameters r=7.7 mm and f=31.2181 mm, each of the various embodiments shown in FIG. 8 must have a back vertex power of about 19.00 diopters for emmetropia in the model aphakic eye. To provide the same amount of accommodation, each of the embodiments of the novel lens must have at least one appropriate mathematically defined aspheric surface of revolution which increases in curvature and refractive power peripheralward.

In FIG. 8a, the posterior or back surface of the novel lens is plane; the anterior or front surface is aspheric and is defined by the following polynomial:

$$y=(16.5236x+8x^2)^{\frac{1}{2}}=2.3014x^{1.5548}+1.2x^{2.3}.$$

In FIG. 8b, the back surface of the novel lens is spherical; the front surface is aspheric and is defined by the following polynomial:

$$y=(26.383x+8x^2)^{\frac{1}{2}}-4.14162x^{1.525}+5.3x^{2.34}.$$

In FIG. 8c, the front surface of the novel lens is aspheric and is defined by the following polynomial:

$$y=(42.7586x+8x^2)^{\frac{1}{2}}-4.6038x^{1.525}+6.7x^{2.3}-8x^5,$$

the back surface is aspheric and is defined by the following polynomial:

$$y=(26.4628x+8x^2)^{\frac{1}{2}}-0.1865x^{1.525}.$$

In FIG. 8d, the front surface of the novel lens is plane; the back convex surface is aspheric and is defined by the following polynomial:

$$y=(16.3158x-x^2)^{\frac{1}{2}}-5.6318x^{1.8}+5.95x^{22}-3x^5.$$

In FIG. 8e, the front convex surface of the novel lens is spherical; the back convex surface is aspheric and is defined by the following polynomial:

$$y=(26.4628x+8x^2)^{\frac{1}{2}}-4.6649x^{1.525}+7.3709x^{2.3}-9x-5.$$

In FIG. 8f, the back surface is concave spherical: the front convex surface is aspheric and is defined by the following polynomial:

$$y=(14.091x)^{\frac{1}{2}}-1.115x^{1.5548}+1.2x^{2.3}-0.5x^5.$$

All of the embodiments shown in FIGS. 8a through 8f can provide accommodation when implanted in the model aphakic eye which is rendered emmetropic. However, the embodiment shown in FIG. 8e is the preferred embodiment which embodiment has been utilized as the example more fully discussed in this specification, and which embodiment is utilized in the preferred lens series of this invention.

In Table 3 I have listed for a series of selected average diameters, b, of the cone-wedge of light at the front surface of this example novel lens implanted in the model aphakic eye, the distances in centimeters of the corresponding sharply focused object planes, and the corresponding amount of accommodation in diopters provided by the novel lens for each of said object plane distances, where the amount of accommodation is determined by taking the reciprocal of the object plane distance in meters. It is to be noted that the selected series of cone-wedge average diameters is only for illustration and is not meant to imply that accommodation is supplied only in discrete steps; in fact, the accommodation provided by the novel lens of this invention is continuous, regular, and progressive over the entire range from far to near, thereby simulating physiologic accommodation in the phakic eye.

It should be understood that where in the specification I have used the model aphakic eye for description and calculations, it is intended that, because the model aphakic eye is designed to as closely as possible represent the human aphakic eye, one may validly substitute the human aphakic eye for the model aphakic eye with the results as calculated for the model aphakic eye.

It should also be understood that the novel lens can have a diameter between 4.5 mm and 7 mm and may have a center thickness other than the 1 mm value which was used for the convenience of illustration in the specification, and that center thicknesses are generally less than 1 mm, ranging from about 0.65 mm to 1.00 mm. In addition, it should be understood that the distance from the apex of the front surface of the cornea to the front surface of the novel lens can be other than the generally accepted 3.6 mm, for example, 4 mm, without departing from the nature and intent of the invention.

Table 3 which is used to illustrate the principle of the lens series of the novel lens of this invention is likewise not intended as a final version since the values listed in Table 3 have been computed with all lens thicknesses 1 mm, and with a value for the distance of the rovel lens from the apex of the front surface of the cornea 3.6 mm. A modification of either or both of lens thickness and lens distance will cause some modification of the listed values in Table 3.

TABLE 1
LENS SERIES SURVEY

| $r_{out}$ (mm) | $e_{out}$ | $D_{out}$ (diopters) | $D_{cor-}$ effective (diopters) | $r_{in}$ (mm) | $e_{in}$ | $D_{in}$ (diopters) | $D_{cor}$ (diopters) | $D_{aq}$ (diopters) | $D_{eye}$ (diopters) | $i_{aq}$ (mm) | $f$ (mm) |
|---|---|---|---|---|---|---|---|---|---|---|---|
| 6.80000 | 0.50000 | 55.33824 | 56.58968 | 5.66667 | 0.46724 | −66.40588 | −9.81620 | 59.29412 | 49.47792 | 27.00195 | 27.55195 |
| 6.90000 | 0.50000 | 54.53623 | 55.75127 | 5.75000 | 0.47160 | −65.44348 | −9.69221 | 58.43478 | 48.74257 | 27.40930 | 27.95930 |
| 7.00000 | 0.50000 | 53.75714 | 54.93734 | 5.83333 | 0.47593 | −64.50857 | −9.57123 | 57.60000 | 48.02877 | 27.81666 | 28.36666 |
| 7.10000 | 0.50000 | 53.00000 | 54.14683 | 5.91667 | 0.48023 | −63.60000 | −9.45317 | 56.78873 | 47.33556 | 28.22402 | 28.77402 |
| 7.20000 | 0.50000 | 52.26389 | 53.37875 | 6.00000 | 0.48451 | −62.71667 | −9.33792 | 56.00000 | 46.66208 | 28.63139 | 29.18139 |
| 7.30000 | 0.50000 | 51.54795 | 52.63215 | 6.08333 | 0.48876 | −61.85753 | −9.22538 | 55.23288 | 46.00749 | 29.03875 | 29.58875 |
| 7.40000 | 0.50000 | 50.85135 | 51.90615 | 6.16667 | 0.49298 | −61.02162 | −9.11547 | 54.48649 | 45.37102 | 29.44611 | 29.99611 |
| 7.50000 | 0.50000 | 50.17333 | 51.19991 | 6.25000 | 0.49718 | −60.20800 | −9.00809 | 53.76000 | 44.75191 | 29.85347 | 30.40347 |
| 7.60000 | 0.50000 | 49.51316 | 50.51263 | 6.33333 | 0.50135 | −59.41579 | −8.90316 | 53.05263 | 44.14947 | 30.26084 | 30.81084 |
| 7.70000 | 0.50000 | 48.87013 | 49.84355 | 6.41667 | 0.50549 | −58.64416 | −8.80060 | 52.36364 | 43.56303 | 30.66820 | 31.21820 |
| 7.80000 | 0.50000 | 48.24359 | 49.19197 | 6.50000 | 0.50961 | −57.89231 | −8.70034 | 51.69231 | 42.99100 | 31.07557 | 31.62557 |
| 7.90000 | 0.50000 | 47.63291 | 48.55721 | 6.58333 | 0.51370 | −57.15949 | −8.60229 | 51.03797 | 42.43569 | 31.48294 | 32.03294 |
| 8.00000 | 0.50000 | 47.03750 | 47.93861 | 6.66667 | 0.51777 | −56.44500 | −8.50639 | 50.40000 | 41.89361 | 31.89030 | 32.44030 |
| 8.10000 | 0.50000 | 46.45679 | 47.33558 | 6.75000 | 0.52181 | −55.74815 | −8.41257 | 49.77778 | 41.36521 | 32.29767 | 32.84767 |
| 8.20000 | 0.50000 | 45.89024 | 46.74754 | 6.83333 | 0.52583 | −55.06829 | −8.32076 | 49.17073 | 40.84997 | 32.70504 | 33.25504 |
| 8.30000 | 0.50000 | 45.33735 | 46.17392 | 6.91667 | 0.52982 | −54.40482 | −8.23090 | 48.57831 | 40.34741 | 33.11241 | 33.66241 |
| 8.40000 | 0.50000 | 44.79762 | 45.61421 | 7.00000 | 0.53379 | −53.75714 | −8.14293 | 48.00000 | 39.85707 | 33.51978 | 34.06978 |
| 8.50000 | 0.50000 | 44.27059 | 45.06791 | 7.08333 | 0.53773 | −53.12471 | −8.05680 | 47.43529 | 39.37850 | 33.92715 | 34.47715 |
| 8.60000 | 0.50000 | 43.75581 | 44.53454 | 7.16667 | 0.54166 | −52.50698 | −7.97244 | 46.88372 | 38.91128 | 34.33452 | 34.88452 |
| 8.70000 | 0.50000 | 43.25287 | 44.01364 | 7.25000 | 0.54556 | −51.90345 | −7.88981 | 46.34483 | 38.45502 | 34.74189 | 35.29189 |
| 8.80000 | 0.50000 | 42.76136 | 43.50479 | 7.33333 | 0.54943 | −51.31364 | −7.80885 | 45.81818 | 38.00934 | 35.14926 | 35.69926 |

TABLE 2

| $r_{out}$ = 6.8 mm | | $r_{out}$ = 7.6 mm | | $r_{out}$ = 7.7 mm | | $r_{out}$ = 7.8 mm | | $r_{out}$ = 8.8 mm | |
|---|---|---|---|---|---|---|---|---|---|
| $l_{ultra}$ (mm) | BVP (diopters) | $l_{ultra}$ (mm) | BVP (diopters) | $l_{ultra}$ (mm) | BVP (diopters) | $l_{ultra}$ (mm) | BVP (diopters) | $l_{ultra}$ (mm) | BVP (diopters) |
| 22.49 | 15.42 | 25.16 | 13.25 | 25.49 | 13.00 | 25.83 | 12.76 | 29.28 | 10.63 |
| 22.37 | 15.92 | 24.99 | 13.75 | 25.32 | 13.50 | 25.66 | 13.26 | 29.05 | 11.13 |
| 22.24 | 16.42 | 24.83 | 14.25 | 25.16 | 14.00 | 25.49 | 13.76 | 28.82 | 11.63 |
| 22.12 | 16.92 | 24.67 | 14.75 | 24.99 | 14.50 | 25.32 | 14.26 | 28.59 | 12.13 |
| 22.00 | 17.42 | 24.51 | 15.25 | 24.83 | 15.00 | 25.15 | 14.76 | 28.37 | 12.63 |
| 21.88 | 17.92 | 24.36 | 15.75 | 24.67 | 15.50 | 24.99 | 15.26 | 28.15 | 13.13 |
| 21.77 | 18.42 | 24.21 | 16.25 | 24.52 | 16.00 | 24.82 | 15.76 | 27.94 | 13.63 |
| 21.65 | 18.92 | 24.06 | 16.75 | 24.36 | 16.50 | 24.67 | 16.26 | 27.73 | 14.13 |
| 21.54 | 19.42 | 23.91 | 17.25 | 24.21 | 17.00 | 24.51 | 16.76 | 27.52 | 14.63 |
| 21.42 | 19.92 | 23.77 | 17.75 | 24.06 | 17.50 | 24.35 | 17.26 | 27.32 | 15.13 |
| 21.31 | 20.42 | 23.62 | 18.25 | 23.91 | 18.00 | 24.20 | 17.76 | 27.12 | 15.63 |
| 21.20 | 20.92 | 23.48 | 18.75 | 23.77 | 18.50 | 24.05 | 18.26 | 26.93 | 16.13 |
| 21.09 | 21.42 | 23.34 | 19.25 | 23.62 | 19.00 | 23.91 | 18.76 | 26.73 | 16.63 |
| 20.99 | 21.92 | 23.21 | 19.75 | 23.48 | 19.50 | 23.76 | 19.26 | 26.54 | 17.13 |
| 20.88 | 22.42 | 23.07 | 20.25 | 23.34 | 20.00 | 23.62 | 19.76 | 26.36 | 17.63 |
| 20.78 | 22.92 | 22.94 | 20.75 | 23.21 | 20.50 | 23.48 | 20.26 | 26.17 | 18.13 |
| 20.68 | 23.42 | 22.81 | 21.25 | 23.07 | 21.00 | 23.34 | 20.76 | 25.99 | 18.63 |
| 20.57 | 23.92 | 22.68 | 21.75 | 22.94 | 21.50 | 23.20 | 21.26 | 25.82 | 19.13 |
| 20.47 | 24.42 | 22.55 | 22.25 | 22.81 | 22.00 | 23.07 | 21.76 | 25.64 | 19.63 |
| 20.37 | 24.92 | 22.42 | 22.75 | 22.68 | 22.50 | 22.93 | 22.26 | 25.47 | 20.13 |
| 20.28 | 25.42 | 22.30 | 23.25 | 22.55 | 23.00 | 22.80 | 22.76 | 25.30 | 20.63 |
| 20.18 | 25.92 | 22.18 | 23.75 | 22.43 | 23.50 | 22.67 | 23.26 | 25.14 | 21.13 |
| 20.08 | 26.42 | 22.06 | 24.25 | 22.30 | 24.00 | 22.55 | 23.76 | 24.97 | 21.63 |
| 19.99 | 26.92 | 21.94 | 24.75 | 22.18 | 24.50 | 22.42 | 24.26 | 24.81 | 22.13 |
| 19.90 | 27.42 | 21.82 | 25.25 | 22.06 | 25.00 | 22.30 | 24.76 | 24.66 | 22.63 |

$l_{ultra}$ = ULTRA SOUND LENGTH
BVP = BACK VERTEX POWER

TABLE 3
CONE-WEDGE DIAMETER AT FRONT SURFACE OF NOVEL LENS AND CORRESPONDING OBJECT PLANE DISTANCE (cm) AND CORRESPONDING ACCOMMODATION IN diopters

| DIAMETER (mm) | OBJECT PLANE DISTANCE (cm) | ACCOMMODATION (diopters) |
|---|---|---|
| .2 | 10309.00 | 0.01 |
| .4 | 2558.00 | 0.04 |
| .6 | 1120.00 | 0.09 |
| .8 | 625.00 | 0.16 |
| 1.0 | 398.00 | 0.25 |
| 1.2 | 276.00 | 0.36 |
| 1.4 | 202.00 | 0.49 |
| 1.6 | 155.00 | 0.64 |
| 1.8 | 123.00 | 0.81 |
| 2.0 | 99.96 | 1.00 |
| 2.2 | 83.20 | 1.20 |

TABLE 3-continued
CONE-WEDGE DIAMETER AT FRONT SURFACE OF NOVEL LENS AND CORRESPONDING OBJECT PLANE DISTANCE (cm) AND CORRESPONDING ACCOMMODATION IN diopters

| DIAMETER (mm) | OBJECT PLANE DISTANCE (cm) | ACCOMMODATION (diopters) |
|---|---|---|
| 2.4 | 70.63 | 1.42 |
| 2.6 | 61.04 | 1.64 |
| 2.8 | 53.63 | 1.86 |
| 3.0 | 47.88 | 2.09 |
| 3.2 | 43.42 | 2.30 |
| 3.4 | 40.00 | 2.50 |
| 3.6 | 37.44 | 2.67 |
| 3.8 | 35.61 | 2.81 |
| 4.0 | 34.41 | 2.91 |

It is claimed:

1. An intraocular lens for the correction of the axial refractive error and the accommodative insufficiency of the post-surgical aphakic eye, made of homogeneous transparent optical material, for placement in the posterior chamber of the human aphakic eye, of continuously and regularly increasing refractive power peripheralward, of a diameter between 4.5 mm and 7 mm and of thickness between 0.65 mm and 1 mm, with at least one surface of said intraocular lens a positive aspheric surface of revolution having an apical umbilical point at which the derivative of curvature vanishes, said surface increasing continuously and regularly in curvature and refractive power from said apical umbilical point to its periphery and where the magnitude and shape of said surface is defined mathematically by means of the following expression:

$$y = (Ax + Bx^2)^{\frac{1}{2}} + Cx^{(p)} + Dx^{(q)} + Ex^{(z)},$$

where $A = 2r_{apex}$, $B = (e^2 - 1)$, e being the eccentricity at the apex of said surface, where C, D, and E are integral or non-integral coefficients of $x^{(p)}$, $x^{(q)}$, and $x^{(z)}$ respectively, and where p, q, and z can be integral or non-integral exponents of x, and where r ranges from 5 mm to 150 mm, where e ranges from 0.0 to 4.0, where at least one of the values of C, D, and E is other than zero, values of C, D, and E ranging from 0.0 to ±9, the values of p, q, and z range from a value of 0.5 to 6.0.

2. An intraocular lens as in claim 1 wherein said one positive aspheric surface of revolution is the front surface of the lens and the back surface is plane.

3. An intraocular lens as in claim 1 wherein said positive aspheric surface of revolution is the back surface of the lens and the front surface is plane.

4. An intraocular lens as in claim 1 wherein said one positive aspheric surface of revolution is the front surface of the lens and the back surface is convex spherical.

5. An intraocular lens as in claim 1 wherein said one positive aspheric surface of revolution is the back surface of the lens and the front surface is convex spherical.

6. An intraocular lens as in claim 1 wherein both front and back surfaces are positive aspheric surfaces of revolution of increasing refractive power peripheralward.

7. An intraocular lens as in claim 1 wherein said one positive aspheric surface of revolution is the front surface of the lens and the back surface is concave.

8. A series of intraocular lenses, each lens in said series coming within the specification of claim 1, said series of lenses subdivided into at least 21 subsets, each of said subsets corresponding to a given apical radius of curvature r of the front surface of the cornea, said apical radius of curvature r ranging from 6.8 mm to 8.8 mm in steps of no more than 0.1 mm, there being at least 25 lenses in each subset sequentially arranged in accordance with values of increasing back vertex power from a lowest value to a highest value of at least 12 diopters greater than said lowest value, the increment of back vertex power separating the lenses in said subset being not greater than 0.50 diopters, each lens of given back vertex power designed to correct the axial refractive error of a given length eye within the specified subset, there being at least 12 lenses for eyes shorter than the average normal length of the eye for said subset value of r, and at least 12 lenses for eyes longer than the average normal length of the eye, there being a total of at least 525 lenses in said series corresponding to at least 525 different combinations of the apical radius of curvature of the anterior surface of the cornea and the axial length of the eye, each lens designed to correct the axial refractive error of the eye in which it is placed and to provide accommodation.

9. A series of intraocular lenses as in claim 8 wherein the front convex surface of the lens increases continuously and regularly in curvature and refractive power from its axis peripheralward and the back surface is plane.

10. A series of intraocular lenses as in claim 8 wherein the front convex surface of the lens increases continuously and regularly in curvature and refractive power from its axis peripheralward and the back surface is convex spherical.

11. A series of intraocular lenses as in claim 8 wherein both the front and the back convex surfaces of the lens increase continuously and regularly in curvature and refractive power from its axis peripheralward.

12. A series of intraocular lenses as in claim 8 wherein the back convex surface of the lens increases continuously and regularly in curvature and refractive power from its axis peripheralward and the front surface is plane.

13. A series of intraocular lenses as in claim 8 wherein the back surface of the lens increases continuously and regularly in curvature and refractive power from its axis peripheralward and the front surface is spherical.

14. A series of intraocular lenses as in claim 8 wherein the front convex surface of the lens increases continuously and regularly in curvature and refractive power from its axis peripheralward and the back surface is concave.

15. A method of selection and obtaining of an appropriate intraocular lens from a given lens series of at least 525 lenses of a given front and back surface design relation, wherein each lens is designed to correct both the axial refractive error and the deficiency of accommodation of an aphakic eye having a given apical radius of curvature r of the front surface of the cornea, and a given length l, of the eye as measured along its geometrical axis from the apex of said corneal surface to the internal limiting membrane of the retina, said method consisting in the utilization of the r and l values in the selection and supply of lenses corresponding to said r and l parameters by the supplier who obtains the appropriate lens from an inventory of at least said 525 lenses, the lens delivered to the doctor being designated by the same r and l values supplied by the doctor and being designed specifically to correct the axial refractive error and the deficiency of accommodation for an eye having said r and l values.

* * * * *